(12) United States Patent
Hwang et al.

(10) Patent No.: US 7,095,507 B1
(45) Date of Patent: Aug. 22, 2006

(54) METHOD AND APPARATUS USING MICROSCOPIC AND INTERFEROMETRIC BASED DETECTION

(75) Inventors: Shiow-Hwei Hwang, Livermore, CA (US); Nat Ceglio, Pleasanton, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 327 days.

(21) Appl. No.: 10/673,058

(22) Filed: Sep. 26, 2003

Related U.S. Application Data

(60) Provisional application No. 60/414,750, filed on Sep. 27, 2002.

(51) Int. Cl.
*G01B 11/02* (2006.01)

(52) U.S. Cl. .................. 356/512; 356/511; 356/516

(58) Field of Classification Search .......... 356/72, 356/450, 511, 512, 73, 516, 496, 503, 504, 356/508, 498
See application file for complete search history.

(56) References Cited

U.S. PATENT DOCUMENTS

| | | | | |
|---|---|---|---|---|
| 4,818,110 A | * | 4/1989 | Davidson | 356/512 |
| 5,112,129 A | | 5/1992 | Davidson et al. | |
| 5,471,303 A | * | 11/1995 | Ai et al. | 356/497 |
| 5,572,598 A | * | 11/1996 | Wihl et al. | 382/144 |
| 5,583,639 A | * | 12/1996 | Rostvall | 356/512 |
| 6,078,392 A | | 6/2000 | Thomas et al. | 356/457 |
| 6,262,818 B1 | | 7/2001 | Cuche et al. | 359/9 |
| 6,480,285 B1 | | 11/2002 | Hill | |
| 6,873,354 B1 | | 3/2005 | Dai et al. | |

OTHER PUBLICATIONS

U.S. Appl. No. 10/672,298, filed Sep. 26, 2003, Office Action dated Nov. 16, 2005.

\* cited by examiner

*Primary Examiner*—Hwa (Andrew) Lee
*Assistant Examiner*—Marissa J Detschel
(74) *Attorney, Agent, or Firm*—Beyer Weaver & Thomas, LLP

(57) ABSTRACT

An integrated interferometric and intensity based microscopic inspection system inspects semiconductor samples. A switchable illumination module provides illumination switchable between interferometric inspection and intensity based microscopic inspection modes. Complex field information is generated from interference image signals received at a sensor. Intensity based signals are used to perform the microscopic inspection. The system includes at least one illumination source for generating an illumination beam and an integrated interferometric microscope module for splitting the illumination beam into a test beam directed to the semiconductor sample and a reference beam directed to a tilted reference mirror. The beams are combined to generate an interference image at an image sensor. The tilted reference mirror is tilted with respect to the reference beam that is incident on the mirror to thereby generate fringes in the interference image. The system also includes an image sensor for acquiring the interference image from the inteferometric microscope module and intensity signals from the microscopic inspection image.

15 Claims, 14 Drawing Sheets

Mirror tilted in the x direction.
Stage scans in the x direction also.

Mirror tilted in the x direction.
Stage scans in the y direction.

METHOD AND APPARATUS USING MICROSCOPIC AND INTERFEROMETRIC BASED DETECTION

CROSS-REFERENCE TO RELATED APPLICATIONS

This application claims priority of U.S. Provisional Patent Application No. 60/414,750, filed 27 Sep. 2002, which application is incorporated herein by reference in its entirety for all purposes. This application is filed concurrently with and related to the following patent application: United States Nonprovisional application Ser. No. 10/672,298, entitled "METHOD AND APPARATUS USING INTERFEROMETRIC METROLOGY FOR HIGH ASPECT RATIO INSPECTION" naming Hwang et al. as inventors. The above-referenced United States patent application is incorporated herein by reference in its entirety for all purposes.

BACKGROUND OF THE INVENTION

The present invention relates generally to methods and systems for inspecting defects on wafers, masks, and reticles. More particularly, the present invention relates to optical inspection systems and techniques.

In a conventional optical inspection system, defects are detected by subtracting a reference image from a test image to produce a difference image. The test image is an optical image of an area on the photomask. The reference image may be an optical image of a similar area on an identical die or on the same die or rendered from a design database. The grayscale residues, i.e., portions of the difference image having a value other than zero, may represent defects in the inspected sample.

Conventional optical metrology techniques use intensity based or scattering based systems. With intensity based systems it is difficult to detect defects sitting in dark structures. Examples of dark structures include the trenches of high aspect ratio devices. Because the background is darker, slight perturbations may not easily be discriminated against the background. Furthermore, dark structures provide relatively low signal levels.

For example, and as illustrated in FIG. 1, the intensity 102 of the reflected signal from a contact hole 104 having an aspect ratio of 3:1 is very low in the vicinity of the hole 104. The normalized intensity 106 for the surface areas 108 outside the contact hole 104 is shown in the illustration to be considerably larger. This plot illustrates the reflected intensity profile under normal coherent illumination. Thus, defects residing on the trench floor would be difficult to discriminate against such a low intensity (dark) background as illustrated by intensity level 102. Moreover, other background noise, such as from misalignment between images for example, may mask slight differences in intensity attributable to the defect.

Laser scattering metrology techniques also rely on the interaction between the illumination and the defect structure, and therefore experience similar difficulties in identifying defects in high aspect ratio structures, i.e., high aspect ratio inspection ("HARI"). Device miniaturization trends are expected to exacerbate this problem. As smaller geometries are used, the resulting smaller structures with smaller HARI will be difficult to detect with current tools. Scanning electron microscopy (SEM) techniques are capable of inspecting HARI defects but are unsuitable for inspection inline. SEM techniques are slow, and require that wafers must be taken off line for the inspection.

As described in United States Nonprovisional application Ser. No. 10/672,298, entitled "METHOD AND APPARATUS USING INTERFEROMETRIC METROLOGY FOR HIGH ASPECT RATIO INSPECTION" naming Hwang et al. as inventors, submitted by at least one of the same inventors of the present invention, phase based techniques and inspection systems are capable of identifying subtle defects, i.e., defects which have very little intensity. But phase measurement is not suitable for detecting all defects. Conventional intensity based inspection systems, for example, are more efficient in identifying many defects such as, large defects or other defects producing a large intensity signal. Phase based inspection techniques are especially suitable for small, subtle defects but aren't ideal in the presence of a signal having a strong intensity. Phase measurements in such an application will create an abundance of problems. A large defect may yield only a small phase defect signal. Phase repeats every cycle (i.e., every angular change of 2 pi radians), thus an optical path difference exceeding one cycle may show up as only a small phase difference. Moreover, in identifying such defects, intensity based systems have lower throughputs and are more sensitive to pattern noise.

Accordingly, what is further needed is an inspection system capable of providing conventional intensity based (i.e., brightfield) inspection for defects generating sufficient signal intensities and further capable of providing inspection of defects which generate low intensity signals.

SUMMARY OF THE INVENTION

To achieve the foregoing, and in accordance with the purpose of the present invention, methods and systems are described for interferometric inspection to generate complex field information regarding semiconductor samples coupled with intensity based microscopic inspection.

The complex field information used to determine defects generating low-intensity signals may include either or both of phase and amplitude of the illumination reflected from the sample. The interferometric inspection system splits an illumination beam into two constituent waves or beams, one directed to the wafer and one directed to a reference surface. The constituent beams combine to form an interference image. Spatial fringes may be created on the interference image by tilting the reference surface, the brightest bands or fringe lines representing points where the constituent waves match in phase.

Perturbations (i.e., departures in the fringe lines from straightness) represent a change in phase or amplitude of the beam reflected from the wafer caused by a change in the structure of the wafer. The change in structure causes a corresponding change in optical path difference between the constituent beams which then result in an observable and measurable change in the fringes of the interference image (i.e., perturbations). The change in structure may be attributable to the design of the configured pattern or other sources including defects. The phase or magnitude determined from the interference image may then be compared with phase or amplitude information from a similar sample, the differences in the comparison used to indicate a defect in the sample. The integrated inspection system permits intensity based inspection on the other portions of the wafer to be performed during a wafer test run and without changing the inspection tool.

The present invention applies interferometric techniques to defect inspection, which is especially suitable for HARI, on semiconductor wafers in combination with intensity-based techniques. The interferometric techniques, as employed in embodiments of the present invention, can identify even subtle defects, such as those that generate very small intensity differences in comparison to the background. The phase-based techniques may be applied, for example, to wafers, masks, or reticles but are generally most suitable in detecting defects where the defects generate small intensity differences relative to a background. The integrated inspection tool also permits inspection using intensity based techniques for more distinct defects. Intensity based techniques are also less sensitive to process noise.

In one embodiment, the present invention provides an inteferometric inspection system for inspecting semiconductor samples. The system includes an illumination module with at least one illumination source providing illumination for microscopic intensity based inspection illumination and a second beam for interferometric illumination. An integrated interferometric microscope module is configured for both interferometric and intensity based microscopic measurement. In the interferometric mode, the illumination beam is split into a test beam towards a sample and a reference beam towards a reference mirror. The two beams are later combined to form an interference image. That is, the test beam reflected from the sample and the reference beam reflected from the reference mirror are combined to form an interference image on a sensor. The reference mirror is tilted to generate spatial fringes in the interference image. An image sensor generates electrical signals based on the interference image for phase measurement and the intensities of the image projected A processing module generates complex field information from the interference image signal. In one aspect sensors operated in TDI (time-domain integrated) mode are used interferometric measurement using spatial fringe analysis techniques. In another aspect, interference fringe orientation is optimized to assist in defect inspection for repeating pattern structures. That is, orientation of the fringes is selected to produce the best signal in view of the directions of the repeating structure on the semiconductor sample. In yet another aspect, two image acquisition systems are employed to enable simultaneous inspection with both interferometric measurement techniques and a microscopic intensity based inspection mode or alternatively with both broadband and narrowband microscopic inspection.

These and other features and advantages of the present invention will be presented in more detail in the following specification of the invention and the accompanying figures, which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF SPECIFIC EMBODIMENTS

Figure 1:
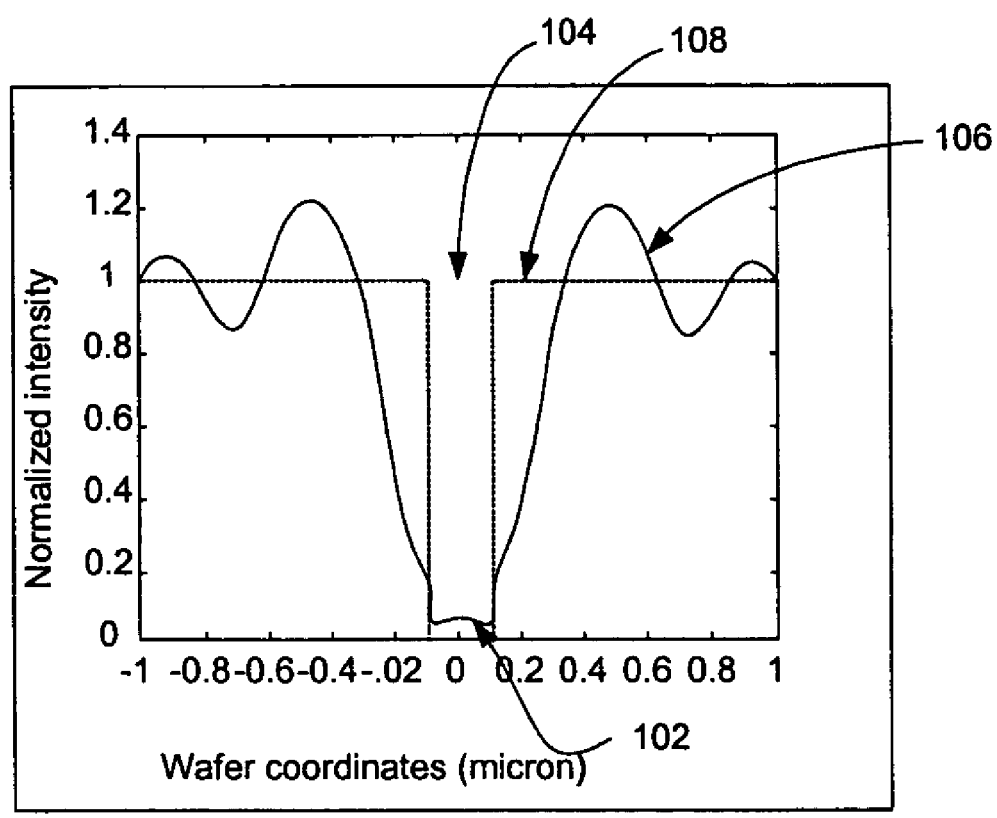
FIG. 1 is a plot illustrating an example of intensity measurements from high aspect ratio structures using conventional optical metrology systems with a coherent source.

Reference will now be made in detail to specific embodiments of the invention. Examples of these embodiments are illustrated in the accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

The present invention applies interferometric techniques to defect inspection on semiconductor wafers. Interferometric techniques have been found to be especially effective for High Aspect Ratio Inspection (HARI) defect evaluation. These techniques, as employed in embodiments of the present invention, can identify even subtle defects, such as those that generate very small intensity differences in comparison to the background. As described above, HARI defect evaluations present unique problems due to the low signal intensities available. The systems and techniques of the present invention are also useful in detecting defects in all contexts, for example, where the defects generate little intensity difference relative to the background, such as, for example, may be present also in reticles or masks used in semiconductor processing as well as with defects that generate greater signals.

Interferometric techniques operate by measuring the distortions in a wavefront emanating from a sample resulting from combination with a reference beam. The interferometric methods and apparatus described in the present invention are applied in general terms by splitting an illumination beam into a reference beam and a test beam. The test beam reflects off the sample, and the reference beam reflects off a reference mirror. The reflected test beam is combined with the reflected reference beam to produce an interference image or interference signal. A Linnik microscope is an example of such a system used in one embodiment of the present invention to perform in two alternative modes defect evaluation and surface topography measurement. Its operation and use in topographic measurement for semiconductor samples is described in further detail in U.S. Pat. No. 4,818,110, which application is herein incorporated by reference in its entirety. The apparatus and techniques as disclosed in embodiments of the present invention provide inspection capabilities with high sensitivities to defects and are capable of being integrated in-line into the wafer production process. The use of a Linnik configuration is intended to be exemplary and not limiting. The techniques and mechanisms described with reference to the present system may be integrated into any interferometric inspection system.

The present invention uses techniques disclosed in the currently pending United States Nonprovisional application Ser. No. 10/672,298, entitled "METHOD AND APPARATUS USING INTERFEROMETRIC METROLOGY FOR HIGH ASPECT RATIO INSPECTION" naming Hwang et al. as inventors; to construct a tool having a superset capability for detecting the defects on a wafer. By combining microscopic intensity based type inspection and interferometric inspection on one platform, benefits from the speed of the microscopic intensity based imaging systems and the sensitivity of the interferometric type measurement can be combined.

According to one embodiment, two modes of illumination are used, one for phase detection and one for microscopic intensity based type inspection. For example, during the phase detection, the illumination is preferably focused onto the pupil of the imaging objective, thereby creating a collimated illumination to the wafer under inspection. For the microscopic intensity based technique, a focused illumination is created with a predetermined pupil profile, which can be varied from one inspection task to another.

By creating the combined inspection platform and the combined technique, the inspection apparatus can be switched from microscopic intensity based type inspection to phase type detection/measurement with the switching of the illumination mode and the shuttering off of the reference module.

According to a preferred embodiment, the imaging sensor for the inspection apparatus is operated in a frame mode with flash on the fly type of illumination scheme or alternatively in time delay integrated mode (TDI) with line scanning implemented by the stage. In using the TDI type sensing scheme for phase measurement, during scanning the invention uses alternative techniques to maintain a constant optical path difference between the reference and the corresponding spot under inspection. In one embodiment, image sensors are operated in TDI mode for interferometric measurement with spatial fringe analysis technique. According to another embodiment, the tilt direction of the reference mirror is adjusted to align with the scanning direction. According to an alternative embodiment, the tilted reference mirror is moved along the z-direction to compensate for the optical path change in the reference arm for each corresponding sensor pixel. According to an alternative embodiment, the interference fringe orientation is optimized to provide higher signal to noise ratios in repeating pattern structures. According to yet another embodiment, two image acquisition systems are used to enable simultaneous inspection with both interferometric measurement technique and microscopic intensity based inspection, or with both broadband and narrowband microscopic inspection.

The following descriptions will explain in detail a combined phase and intensity based inspection system in accordance with specific embodiments of the present invention. A specific embodiment of the present invention provide an inspection apparatus suitable for measuring a variety of defects, including defects providing strong signal intensities and those providing low signal intensities. The latter types of defects are often prevalent in high aspect ratio structures. In accordance with one embodiment of the present invention, the inspection system comprises an illumination module, configured to generate a brightfield (i.e., incoherent) beam for intensity based inspection of wafers and a coherent beam for phase based inspection.

In a preferred embodiment, the invention is constructed with two independent channel of image acquisitions and/or image processing for use with two different wavelength band of illumination, one for the phase measurement and the other for the microscopic intensity based inspection. These two different wavelength bands can be constructed with one single unit that can handle both spectrums and both illumination pupil conditions, or alternatively with two different illumination systems that share some common paths. For example, the invention in one embodiment is constructed to utilize $\lambda 1$ laser or narrowband source for the phase inspection and a broadband source having a wavelength in the range of $\lambda 2$ to $\lambda 3$, wherein the $\lambda 2$ to $\lambda 3$ range excludes $\lambda 1$. By incorporating a dichroic beam-splitter, this embodiment of the invention can easily be operated with both modes on simultaneously. This improves the inspection coverage areas for each mode enables both measurement techniques to be performed simultaneously for the same area.

Also, with this configuration, the system can be operated at solely microscopic intensity based type inspection by switching off the phase measurement mode, but performing the microscopic inspection with both broadband $\lambda 2$ to $\lambda 3$, and narrowband $\lambda 1$. This configuration will allow the user to gain sensitivity in inspection of smaller defects for some structures if $\lambda 1$ is smaller than $\lambda 2$ to $\lambda 3$. That is, in this embodiment, both broadband and narrowband microscopic intensity based inspection can be performed.

Figure 10:
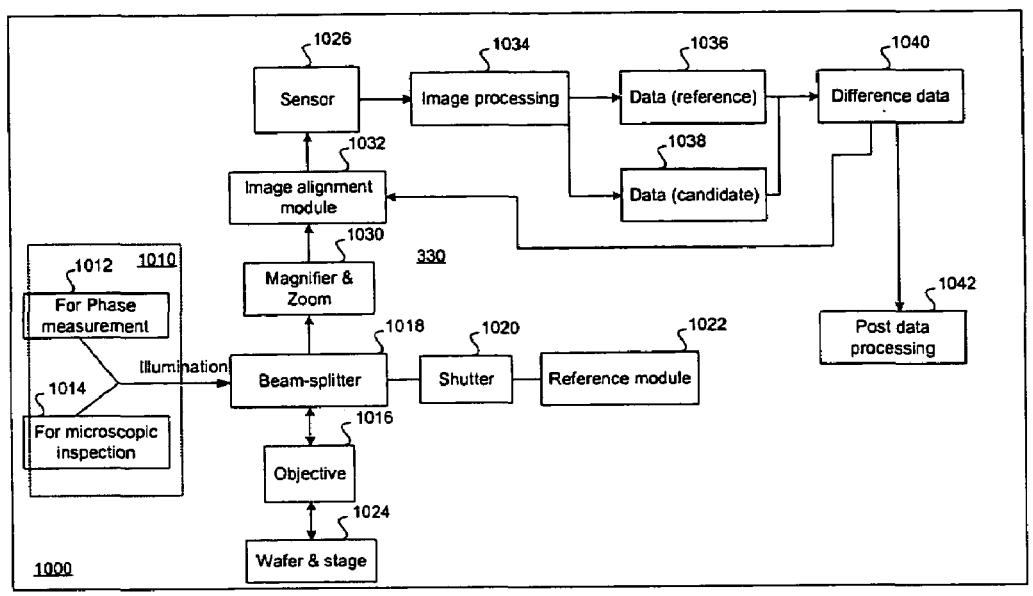
FIG. 10 is a block diagram of an inspection system using microscopy and interferometry in accordance with one embodiment of the present invention.

FIG. 10 is a block diagram of an inspection system 1000 using intensity based microscopy and interferometry inspection in accordance with one embodiment of the present invention. As shown, illumination for the inspection system 1000 is generated in a switchable illumination module 1010.

This embodiment of the present invention may be implemented with any suitable illumination source or sources configured to generate a brightfield illumination beam for intensity based inspection and a coherent illumination beam (e.g., a laser) for phase based inspection. For example, the brightfield illumination may be provided by a white light lamp. The coherent illumination source may include any source having sufficient spatial coherence et to form spatial interference fringes using the configuration of the system. For example, a deep ultraviolet laser is suitable. A phase based illumination beam 1012 and microscopic intensity based inspection illumination beam 1014 are shown generated.

The focusing of the phase detection illumination onto the pupil of the imaging objective lens 1016 distinguishes the two modes of illumination in accordance with one embodiment. Here, in phased based inspection, the focusing is located at such a position so as to create a collimated (converging) illumination of the wafer under inspection. Configurations of an optical lens or group of lenses to create collimated illumination are known in the art and for this reason will not be described further here. Conversely, in the intensity based illumination (i.e., the microscopic inspection technique), the microscopic illumination source is an extended source that provides cone illumination. For example, the microscopic intensity based illumination beam provides focused illumination within a predetermined pupil profile.

The illumination module 1010 provides switchable illumination by any of several methods. For example, multiple illumination sources may be provided with a shared optical path. A white light lamp, for example, may be used for intensity based inspection whereas a deep U.V. laser may be used for phase inspection. A mechanical switch (not shown) may then be used to switch between the sources. Alternatively, a mechanical switch may be provided to switch between two independent optical paths.

As described in some detail above with reference to FIG. 3A and in particular the Linnik module 304, for the phase measurement mode, the incident illumination beam may be split into reference and inspection beams, and later combined to create an interference image or signal on a sensor, such as a CCD. As further illustrated in FIG. 10, the beam splitter 1018 performs the splitting function, directing the reference beam in the direction of the shutter 1020 and reference module 1022, and the inspection beam toward the wafer 1024. As described above, the beam splitting function may be performed by a dichroic mirror or by other known methods in the optical industry. The reference and inspection beams are then reflected respectively from the reference mirror (not shown in FIG. 10, but included within the reference module 1022 as generally described above with reference to FIG. 3A) and the wafer and subsequently recombined to generate an interference image at the sensor 1026. The method of generating interference fringes, such as by tilting the reference mirror, occurs in one embodiment in a similar manner to that described above with reference to FIGS. 3A and 3B. That is, the reference mirror may be tilted so that destructive and constructive interference nodes are spread over the surface of the CCD. Thus, it can be seen that the reference module here functions to provide interferometric measurement techniques for phase based inspection.

Shutter 1020 functions to isolate reference module 1022 from the reference beam when the system 1000 is operating in an intensity-based inspection mode. The shutter 1020 may comprise any suitable mechanism for impeding the reference beams from reaching and reflecting from the reference module 1022. Shutter mechanisms and shutter control mechanisms (not shown) used in optical paths are known to those of skill in the art and further description is believed unnecessary. Thus, in the microscope intensity based inspection mode, no interference images (e.g. interferograms) will be formed on the sensor 1026, and accordingly, conventional microscope inspection proceeds based on the intensities measured at sensor 1026.

Phase based inspection techniques typically require illumination sources that are both spatially and temporally coherent. For microscopic inspection (i.e., intensity-based inspection), typically the illumination source is both spatially and temporally incoherent. Generally, incoherent illumination sources are more suitable for intensity-based inspections. Since coherent illumination will produce bands of light interference (i.e., diffraction effects) that will interfere with the integrity of the defect signals, coherent sources are generally not well suited for intensity-based inspection. Thus, by providing an inspection system including a switchable illumination module, the present embodiment of the invention provides the capabilities of using the same inspection system to inspect a wide variety of defects, e.g. large and small, distinct and subtle, by selecting either intensity based, phase based, or both inspection modes for inspection of a particular area of a wafer. With this arrangement, the switching may be accomplished in a matter of seconds by the switching of the illumination mode and the shuttering off of the reference module in accordance with one embodiment.

As a further alternative, one embodiment of the present invention employs two different wavelength bands of illumination. This embodiment may be constructed using a single inspection unit, or with two different illumination systems that only share some optical elements. For example, phase inspection may be implemented using a laser or other narrowband source having a wavelength $\lambda 1$. Microscopic intensity based inspection may then be performed using a broadband source with a wavelength covering the range $\lambda 2$–$\lambda 3$, but excluding $\lambda 1$. With this arrangement, it is possible to use a dichroic beam splitter to operate the system or systems simultaneously. That is, the present embodiment of the invention may be operated such that both modes are on. Thus, this arrangement improves the inspection coverage areas for each mode. This arrangement also permits both measurement techniques to be performed simultaneously for the same area of the wafer.

In some special cases, such as, for example, the inspection of smaller defects or structures, the use of a temporally coherent illumination source is desirable to provide increased sensitivity for intensity based inspection. The arrangement described above may be modified to utilize both the broadband source (i.e., $\lambda 2$–$\lambda 3$) and the narrowband source (i.e., $\lambda 1$) with the phase measurement mode switched off. This may be accomplished by shuttering off the reference module 1022 while allowing both illumination sources to direct beams to the wafer. With this arrangement, increased sensitivity for intensity based inspection is accomplished as a result of the lower wavelength of the narrowband source.

The inspection system 1000, according to one embodiment, also includes magnifier and zoom module 1030, image alignment module 1032, image processing module 1034, reference data module 1036, candidate data module 1038, difference data module 1040 and post data processing module 1042. Each of these modules is substantially similar in construction and function to the modules described below with reference to FIGS. 3A and 3B. For example, as above, the magnifier and zoom module 1030 is arranged in the optical path between the beamsplitter 1018 and the image sensor 1026 for providing fine adjustment of the magnification from the wafer or other sample to the image sensor. Any suitable type of magnifier and zoom component may be used within the inspection system 1000.

By integrating interferometric measurement with microscopic type intensity based inspection into one platform, both types of measurement may be performed during each wafer inspection run. For example, the wafer or die may be segmented into different types of regions. One type may optimally be inspected with intensity based microscopic techniques and the other with interferometric types of measurements.

Two common methods for acquiring image signals from a sensor involve frame mode and time domain integrated modes (TDI). The TDI mode is commonly used for brightfield (intensity based) inspection and provides high stability and throughput. The frame or flash on the fly mode is better suited for phase measurement than the TDI mode since no compensation in the reference beam optical path is required as a result of the scan movement. In order to minimize the switching times between one mode to the other and to minimize the structure of the integrated inspection system, the sensor mode selected for the system sensor is preferably adapted to operate in both of the intensity based and phase based modes.

In accordance with one embodiment of the present invention, the imaging sensor 1026 for the inspection platform may be operated in a frame (frame-capture) mode. Typically the sensor 1026 is an image sensor, such as a CCD. In the frame mode, the sensor 1026 grabs a frame (i.e., an entire image of the sample) on the fly. Sensors in frame mode are typically used for phase measurement but may be employed without modification for intensity-based measurements. The frame mode, however, lacks the high throughput that can be provided by, for example, the time domain integrated (TDI) mode or the sensitivity to detect low intensity signals capturable by the TDI mode.

To overcome the problems of low throughput and light level of the frame mode in intensity based measurements, the TDI mode is adapted in one embodiment to be used for both phase and intensity based measurements. In the TDI mode, the wafer stage 1024 is configured to perform line scanning. A series of sensor pixel measurements along a line corresponding to a similar line on the wafer are combined (i.e., integrated) to increase the intensity level of the measurement. Electronic circuitry connected to the sensor 1026 outputs is configured to perform the integration. Methods of configuring the output signals to perform the integration are known to those of skill in the art and will not be described further here. The TDI mode, used in a conventional configuration, is not well suited for acquiring phase measurements. Unless the optical path difference between the reference mirror and the corresponding spot on the wafer subject to inspection remains constant, phase measurements will be averaged over the course of the scan, thus washing out the phase information. The present invention provides two alternative embodiments for preserving phase information in a TDI type-sensing scheme.

Figure 11A:
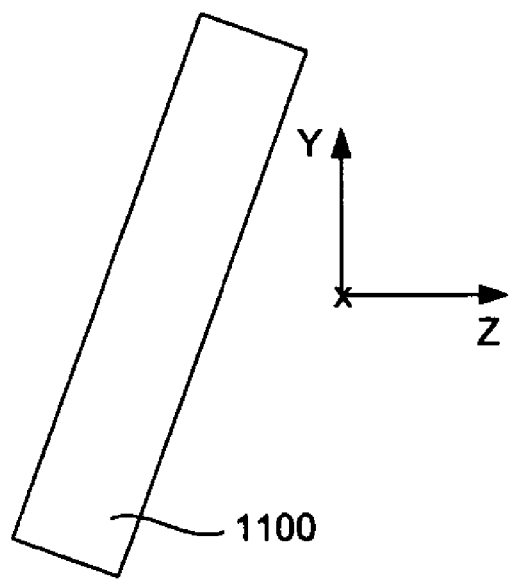
FIG. 11A is a diagram illustrating tilting of a reference mirror of an inspection system in accordance with one embodiment of the present invention.
Figure 11B:
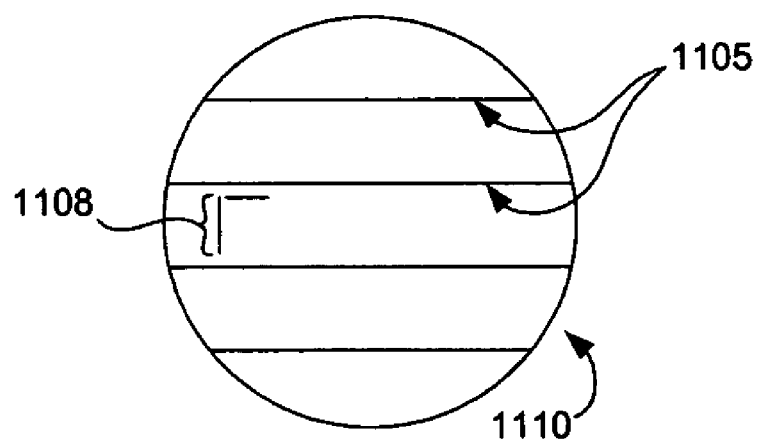
FIG. 11B is a diagram illustrating a sample image appearing on a sensor in accordance with one embodiment of the present invention.

In the first embodiment, the tilt direction of the reference mirror (e.g., located within the reference module) is tilted to correspond to the direction of the stage scan. FIG. 11A is a diagram illustrating tilting of a reference mirror of an inspection system in accordance with one embodiment of the present invention. As illustrated, the reference mirror 1100 is shown titled along the x-axis. In order to maintain a constant OPD, the stage must cause the wafer scanning movement to occur also in the x direction. Stated another way, the tilting of the reference mirror along the x-axis may produce horizontal fringes 1105, as illustrated in the sample image on sensor 1110 depicted in FIG. 11B. FIG. 11B is a diagram illustrating a sample image appearing on a sensor in accordance with one embodiment of the present invention. Thus, alignment of the tilt direction of the reference mirror with the scanning direction x preserves the optical path difference. The stage movement causing the wafer to move in the x-direction will not affect the relative positioning of the fringes with respect to the image of the corresponding structural features on the wafer, such as pattern lines 1108.

Figure 12A:
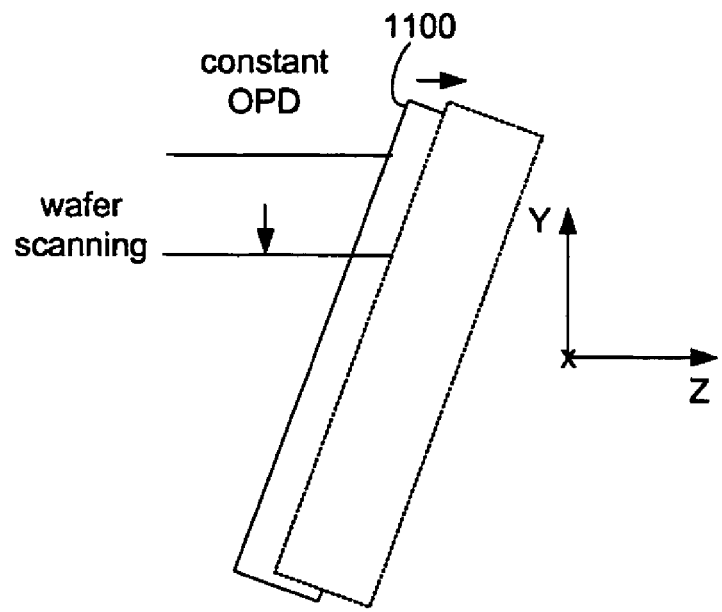
FIG. 12A is a diagram illustrating tilting and movement of a reference mirror of an inspection system in accordance with another embodiment of the present invention.

In a second embodiment employing the sensor TDI mode, optical path difference may be maintained by adjusting the location of the reference mirror in the z-direction to compensate for the optical path change in the reference beam path for each corresponding sensor pixel. FIG. 12A is a diagram illustrating tilting and movement of a reference mirror of an inspection system in accordance with another embodiment of the present invention. As illustrated, the reference mirror 1100 is tilted in the x direction, i.e., about the x-axis. This results in the formation of spatial fringes essentially parallel to a corresponding x axis of the sensor. That is, greater tilting of the mirror 1100 about its x axis increases the spacing between the parallel spatial fringe lines formed on the surface of the sensor while maintaining the direction of the fringe lines as parallel to the sensor's x axis. For purposes of this description, the surface of the sensor lies in the x-y plane of the sensor. In the TDI mode, any scanning movement of the stage supporting the wafer causes a corresponding shift in the location of the structural features on the image projected onto the sensor. If the shift direction is parallel to the spatial fringe interference lines formed on the sensor (i.e., "aligned"), as described above, then phase measurement using the TDI mode may be accomplished without further adapting the system. That is, phase information may be determined by measuring the spatial fringes. For example, the resulting sensor measurements relating to a structural feature on the wafer may be accurately derived (e.g., averaged) from the integrated (i.e., sum) predetermined number of measured values (e.g., 5) for adjacent pixels on the sensor.

But, where the stage scan movement results in a shift in direction of the image on the sensor in the y direction (i.e., perpendicular to the direction of the spatial fringe lines), movement of the reference mirror in the z direction, as illustrated in FIG. 12A, adjusts the OPD for phase measurement and inspection. The movement of the reference mirror is depicted in FIG. 12A by the dotted line representation of the reference mirror in a second position. As a further example, if a single movement of the stage scan causes the location of a structural feature on the image to move from a spatial fringe line to midway between the spatial fringe lines, adjustment of the reference mirror in the z direction location may be performed to cause a similar shift in the spatial fringe lines. It should be noted that any movement a of the reference mirror in the z direction results in a change of 2a in the optical path difference. Hence, in order to cause the spatial fringe lines to shift to a midway position relative to their original locations on the sensor, a shift of $0.25\lambda$ in the z-direction is appropriate. Methods of providing precise movement and control of the reference mirror are known in the art.

Figure 12B:
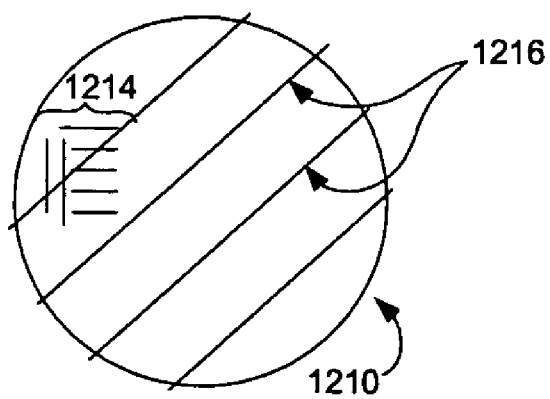
FIG. 12B is a diagram illustrating a sample image appearing on a sensor configured in a time domain integrated mode in accordance with one embodiment of the present invention.

Aligning the reference mirror with the scanning direction may be easily facilitated. But, as the density of circuitry patterns increases, resolution may have to be sacrificed. For example, microelectronic circuitry typically appears in a "Manhattan" pattern, i.e., with patterns formed in both horizontal and vertical directions. Resolving aligned spatial fringe lines in the presence of dense horizontal and vertical pattern lines thus becomes increasingly difficult. FIG. 12B is a diagram illustrating a sample image appearing on a sensor configured in a time domain integrated mode in accordance with one embodiment of the present invention. As shown, pattern 1214 is in such a "Manhattan" pattern, having primarily horizontal and vertical pattern lines. By maintaining the OPD through movement of the reference mirror in the z direction, as described above, the spatial fringe lines may be placed in any orientation. For example, a 45 degree orientation may be selected for a dense "Manhattan" pattern in order to prevent loss of resolution in the phase measurement. The spatial fringe lines 1216 shown in FIG. 12B are thus oriented to optimize the resolution. The 45 degree spatial fringe orientation may be achieved, for example, by tilting the reference mirror 45 degrees along the x-axis and 45 degrees along the y-axis to generate a composite angle of 45 degrees for the spatial fringe lines on the sensor. Thus, the flexibility in placing the spatial fringe lines in any orientation optimizes the resolution available for phase measurement.

Thus, by adapting the system to acquire image signal information from the sensor in TDI mode for either intensity based or phase based inspection, the described embodiments minimize switching time to switch from one mode to another and minimize the structure required for the integrated inspection platform.

Figure 13:
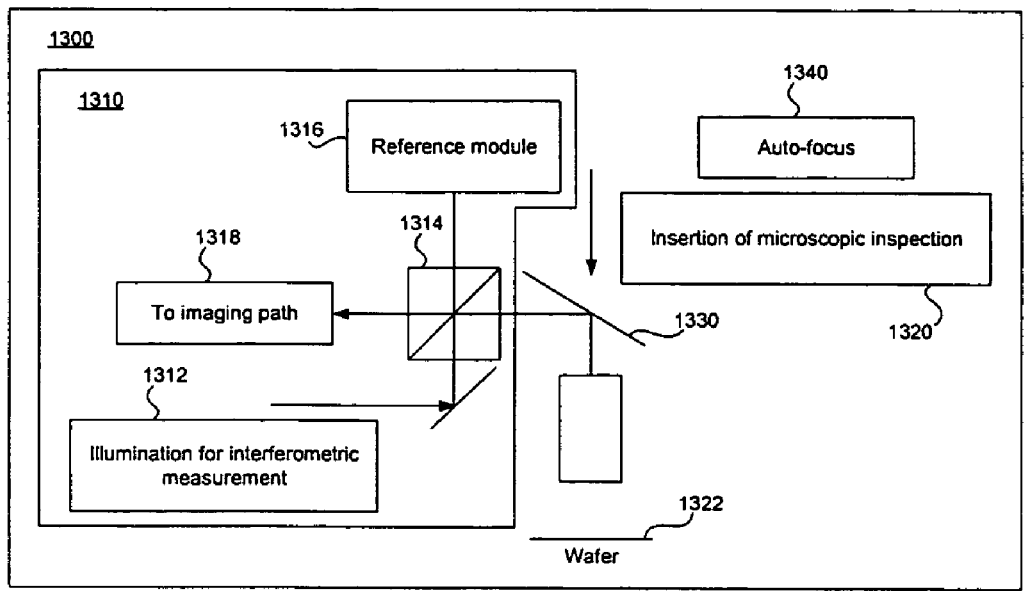
FIG. 13 is a block diagram of an inspection system using intensity based microscopy and interferometry in accordance with one embodiment of the present invention.

FIG. 13 is a block diagram of an inspection system using intensity based microscopy and interferometry in accordance with one embodiment of the present invention. The inspection system 1300 includes a phase measurement module 1310 for performing inteferometric inspection and a microscopic inspection module 1320 for performing intensity based inspection. The phase measurement module 1310 includes an illumination source 1312 for inteferometric measurement, a beam splitter 1314 for separating the illumination beam into an inspection beam and a reference beam, and a reference module 1316 to reflect the reference beam in order to create the spatial fringes, all of which are substantially similar in construction and operation as described above with reference to FIG. 10. The phase measurement module 1310 also creates the spatial fringes on a sensor in the imaging path 1318. It should be noted that the imaging path may contain, in addition to the sensor, other modules such as the magnifier and zoom module and alignment module as described above with reference to FIG. 10. A separate microscope inspection module 1320, having a separate sensor to record measurement, may be integrated into the inspection system in this embodiment using dichroic beam splitter 1330. Thus, the inspection system according to this embodiment may perform measurement techniques simultaneously on the same portion of the wafer 1332 under inspection. By separating the intensity based inspection and phase based inspection onto substantially independent channels, the auto-focus module 1340 may be adjusted to independently focus the microscopic inspection without affecting other modules in the imaging path 1318 for the phase based inspection. For example, the magnifier and zoom module 1030, illustrated in FIG. 10, may thus remain unaffected by the actions of the auto-focus module 1340. Control signals to control the various operations in the inspection process including, for example, the switching, optical path difference adjustments, pattern recognition and image processing may be performed by any suitably configured computer or computers or electronic circuitry. For example, the computer may take the form of an integrated circuit, printed circuit board, handheld computer, or any general purpose computer without limitation.

Figure 2:
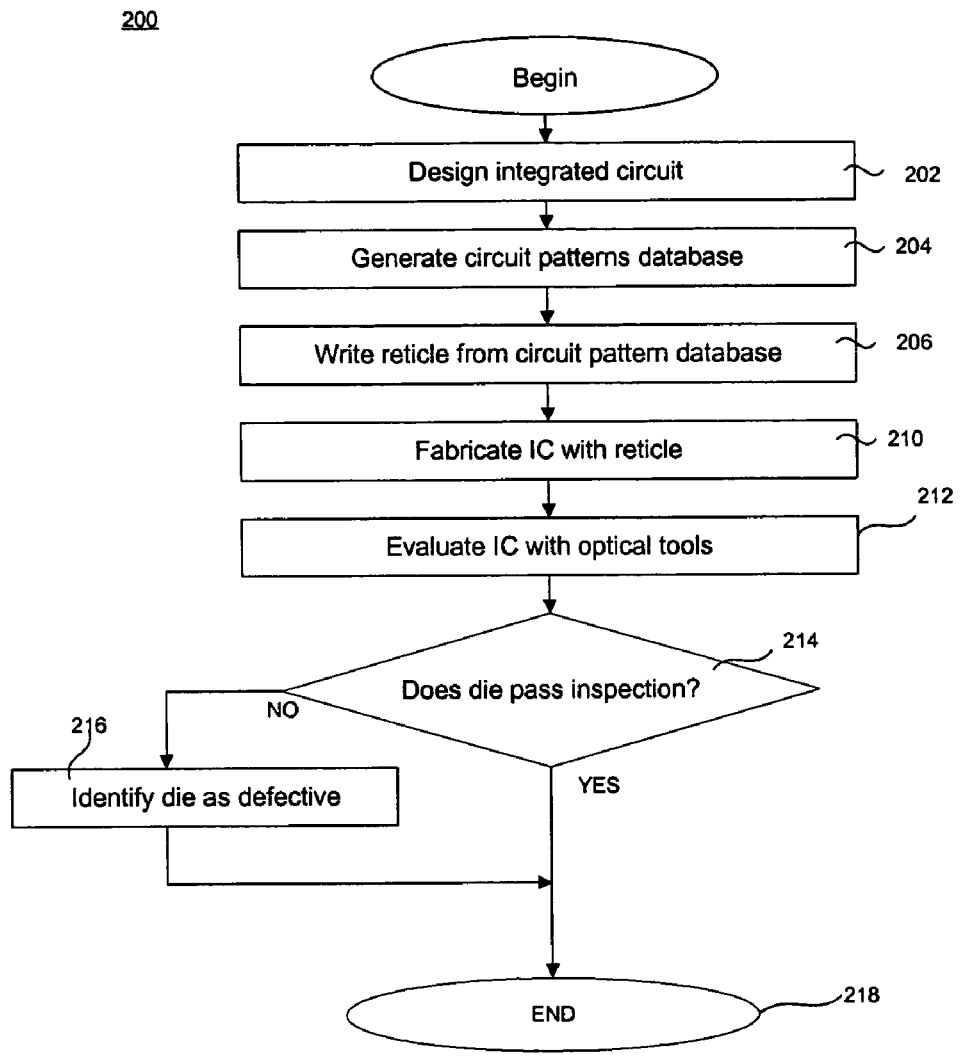
FIG. 2 is a flowchart illustrating an inspection of a sample in accordance with one embodiment of the present invention.

FIG. 2A is a flowchart illustrating a conceptual flow of an integrated circuit design process 200 and an inspection process used to identify defects in the fabricated dies in accordance with one embodiment of the present invention. Initially, in operation 202, an integrated circuit (IC) device is designed using any suitable design techniques. For example, an IC designer may use preexisting schematic library blocks to form the IC device using, for example, electronic design automation (EDA) tools. In some cases, the IC designer may create the IC device or part of the IC device from scratch with the aid of any suitable design system, such as conventional computer aided design (CAD) tools. For example, the IC designer may use a schematic CAD tool to plan the logic diagrams for a particular IC device. Still further, the IC designer may write a description of the IC device or portions of the IC device with the aid of a hardware design language, such as VHDL.

Next, in operation 204 the IC designer generates a circuit pattern database (commonly referred to as a "layout") from the IC design in operation 204. The circuit pattern database is composed of a plurality of electronic representations of layout patterns for IC layers that are later converted into a plurality of reticles that are used to fabricate a plurality of physical layers of an IC device. Each physical layer of the fabricated IC device corresponds to one of the reticles and an associated one of the electronic representations of the circuit pattern database. For example, one electronic representation may correspond to a diffusion pattern on a silicon substrate, another to a gate oxide pattern, another to a gate polysilicon pattern, another to a contact pattern on an interlayer dielectric, another to a line pattern on a metallization layer, and so on. Each electronic representation is composed of a plurality of polygons or other shapes (herein, referred to as "figures"), which together define the reticles pattern.

The circuit pattern database may be generated using any suitable technique, for example, by using EDA or CAD tools. For example, the IC designer may manually lay out the circuit patterns for the IC device with or without pre-existing library cells. Alternatively, a synthesis tool may automatically create circuit patterns for the IC device from scratch or by piecing together preexisting library cells.

After the circuit pattern database is generated, the circuit pattern database is used to produce a plurality of reticles in operation 206. The reticles may be produced by any suitable pattern generator or reticle writer equipment. Each reticle corresponds to one or more electronic representation(s) from the circuit pattern database. A reticle is then inspected, to determine its suitability for use in fabrication. Any suitable inspection method may be used including optical methods and scanning electron microscope methods. Interferometric inspection methods in accordance with embodiments of the present invention may also be used to perform reticle evaluations. The reticle may then be used to fabricate a physical layer of the IC device in operation 210. Operations 206 through 212 may be implemented for some or all of the electronic representations of the circuit pattern database.

In a step 212, the fabricated integrated circuit is evaluated using optical tools. For example, each of the multiple dies formed on a wafer may be an integrated circuit. Each of the dies may be inspected by the embodiments of the present invention to identify defects. The evaluation may be performed using the interferometric methods described below, including inspection for defects and topographic measurements to measure surface characteristics of the die. In a step 214, a determination is made as to whether the die passes inspection. If the die fails inspection, the die is identified as defective in a step 216. The process ends for that die after inspection and identification of defective dies. Steps 212–216 may be repeated for each of the multiple dies on a wafer.

The mechanisms of the present invention may be implemented on any suitable inspection tools arranged to perform interferometric measurements including those further configured to compare a test sample with a reference sample, such as by comparing a die, with another portion of the die, another die or data in a design database corresponding to the die design. Additionally, the inspection mechanisms of the present invention may be implemented on any other suitable type of semiconductor sample inspection tool.

Figure 3A:
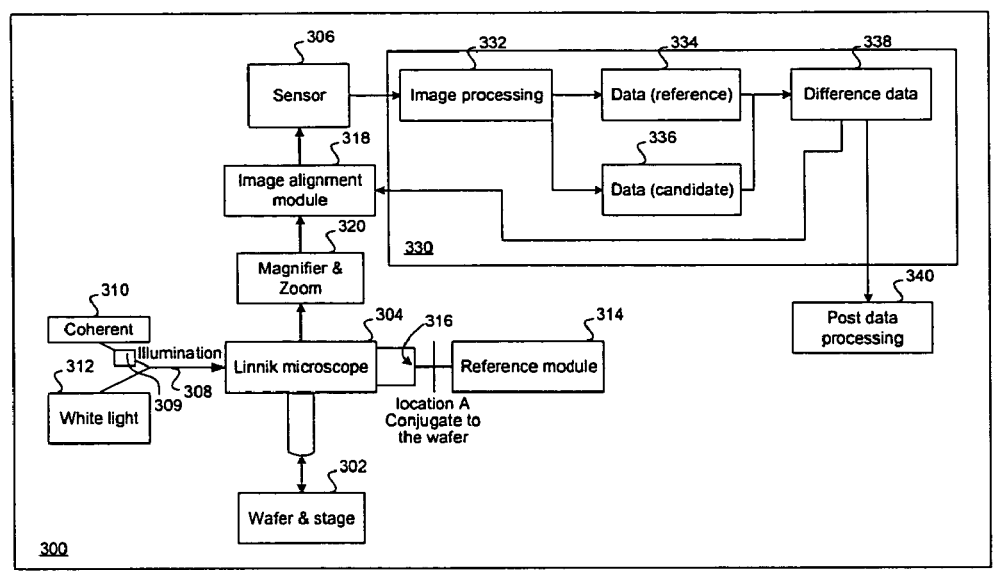
FIG. 3A is a block diagram of an interferometric inspection system in accordance with one embodiment of the present invention.

FIG. 3A is a simplified block diagram illustrating an interferometric inspection system in accordance with one embodiment of the present invention. The interferometric inspection system 300 may be used, for example, to perform the reticle evaluation as described above with reference to step 206 of FIG. 2, or the IC evaluation in step 212. For example, the interferometric inspection system 300 is arranged in one embodiment to inspect an integrated circuit of a wafer present on a stage such as depicted in wafer and stage block 302. The wafer and stage 302 may comprise a wafer or mask or reticle positioned upon a moveable stage to allow controlled movement of the wafer, mask, or reticle with respect to the inspection apparatus.

In general terms, the interferometric inspection system identified in several embodiments of the present invention uses any suitable Linnik microscope 304. A suitable two-beam Linnik microscope is described in further detail in U.S. Pat. No. 4,818,110 (herein referred to as the '110 patent), which is incorporated herein by reference for all purposes. In general, a Linnik microscope 304 is an example of an interferometric inspection apparatus which splits a received illumination beam by a beam splitting device contained within the Linnik microscope 304 into a test beam and a reference beam, e.g., by amplitude division. The test beam is directed to the sample, such as a mask, reticle, or a wafer. The reference beam is directed to a reference surface, such as a mirror. The test beam reflected from the sample and the reference beam reflected from the reference surface are combined in the Linnik microscope to form an interference image at an image sensor 306. An example of such an image sensor is a charge coupled device (CCD), which operates to convert light energy to an electrical signal. The Linnik configuration described in the '110 patent permits topographic measurement, for example to verify critical dimensions. The configuration described with respect to FIGS. 3A and 3B expands those capabilities to provide complex field information to facilitate defect detection.

An illumination beam may be generated by any suitable type of illumination source(s). In the illustrated embodiment, the illumination beam 308 is shown generated by a coherent (white light) light source 310 and an incoherent light source 312. The coherent light source 310 is used generally for determining complex field information (i.e., phase and magnitude) from a sample. Accordingly, the light sources 310 and 312 are individually selectable. The white light source 312 is an incoherent illumination source, used for topographic measurement in one embodiment of the present invention. Methods for using an incoherent illumination source for topographic measurement are described more fully in the above referenced '110 patent. The topographic measurements utilize the short coherence length of the white light illumination source 312 to identify the features of a sample such as a semiconductor wafer, at various levels within the semiconductor wafer structure. Because of the very short coherence length of the white light illumination source, the Linnik microscope in this operational mode acts as a coherence probe having a very limited depth of field, thus suitable for limiting measurement information to a particular level within the wafer. This makes the Linnik system in this configuration ideal for making topographic measurements, for example, of a wafer structure.

In one embodiment, a speckle buster 309 is placed in the path of the illumination beam emanating from a coherent illumination source, for example coherent source 310 as illustrated in FIG. 3A, in order to reduce the spatial coherence of the impinging light for topographic inspection. That is, the speckle buster or "randomizer" in effect randomizes the distribution of the impinging light, and therby eliminating the need for a separate broadband source. Speckle busters are known to those of skill in the relevant art and thus further description here is deemed unnecessary. For example, typical speckle busters comprise rotating circular diffusion elements.

The interferometric inspection system is also configured to operate in a second mode to determine complex field information including phase and amplitude. In this embodiment, reference module 314 is used to generate spatial fringes in the interference image produced at the image sensor 306. For example, a tilted reference mirror is arranged in the module to receive and reflect the reference beam and to create the fringes in the interference image. Alternatively, the reference module 314 may be configured to generate phase shift information through the manipulations of mirrors located in the reference module, i.e., in a phase-shifting mode, as will be described below.

The interferometric inspection system also comprises in one embodiment a dichroic mirror 316, which may optionally be placed at location A for operation of the Linnik 304 as a coherence probe for performing topographic measurement. The dichroic mirror is a partially reflective surface, reflecting a certain spectral range of the incident light but transmitting the remainder. In this embodiment, the arrangement of the dichroic mirror allows switchable operation of the inspection system to either perform topographic measurements, or to generate phase and/or amplitude information from the sample. For example, a coherent illumination beam may be used for the complex field inspection mode, and an incoherent illumination beam is used for the topographical metrology mode. A white light illumination source provides some advantages over coherent sources in topographic measurements due to its short depth of field. As known to those of skill in the art, the intensity of spatial fringes in an interference image decreases as the optical path difference "OPD" (i.e., the difference in lengths between the optical paths of the reference beam and the test beam) approaches the coherence limit (i.e., the OPD where the phase information is no longer recoverable). Thus, the broadband frequencies of the white light source, having a shorter coherence length, have a shorter depth of field which makes a broadband source more suitable for measuring the pattern features at a selected surface of a semiconductor structure because spatial fringes are minimized in the interference image.

When operating in the topographic measurement mode, reflection of the undesirable light (i.e., light transmitted through the dichroic surface 316 and reflected back from the tilted mirror of the reference module 314 and back to the interference image), may alternatively be blocked by a shutter incorporated in the reference module or anywhere between the tilted mirror in the reference module and the Linnik 304. The undesired reflected light may otherwise "wash out" or dominate the topographic image generated at image sensor 306.

A magnifier and zoom module 320 is arranged in the optical path between the Linnik microscope 304 and the image sensor 306 for providing fine adjustment of the magnification from the wafer or other sample to the image sensor. Any suitable type of magnifier and zoom component may be used within the inspection system 300. A suitable magnification ratio used with a spatial fringe analysis method is selected such that the desired feature size is imaged across four pixels or more. For example, wafer processing technologies embodying critical dimensions of 0.13 micron in width would be magnified such that the critical dimension (i.e., the 0.13 micron wide line) would be imaged across at least 4 pixels. The magnifier and zoom module 320 provides a fine adjustment to the magnification generated by the magnifier. For example, a zooming adjustment within the range of −7% to +7% is suitable.

The magnifier and zoom feature is useful for aligning the inspection area of the sample to the image sensor during frame mode inspection, i.e., comparison of one feature in a repeating array with another similar feature in the array to identify defects. For example, an image sensor such as a CCD may be arranged to resolve an optical image transmitted to the sensor into a composite image comprising a plurality of individual picture elements which are commonly identified as pixels. Absent an adjustment mechanism, for example, a pattern line may fall entirely within four pixels of the image sensor 306, but a similar pattern line from the same die used for inspection comparison purposes may straddle five pixels on the image sensor 306, each border of the four pixel wide pattern line encroaching into the first and fifth pixels. Differences between the two pattern lines, for example in a difference image, thus may be solely caused by the misalignment. The fine zooming adjustment is arranged to fine tune the zooming so that the distance between the corresponding borders of the two pattern lines on the image is approximately an integer multiple of the pixel spacing on the image sensor 306. This arrangement permits the performance of frame type inspection with higher sensitivity and generates fewer false defects.

Also illustrated is image alignment module 318. In one embodiment, this module is operable to minimize the alignment error between a test sample (e.g. die) and the reference sample (e.g., a second die), to increase the sensitivity and the throughput by providing an accurate but relatively fast alignment mechanism. The alignment module 318 alters the alignment of the test image with respect to the image sensor 306, to thereby better match the reference image. An electrical feedback signal may be used to determine if further adjustments are necessary to the alignment mechanisms contained within the image alignment module 318 as further described below with reference to FIGS. 6A and 6B.

Furthermore, the inspection system may in one embodiment include a processing block 330 which may be arranged to process the image acquired from the image sensor 306 and thereby generating difference data 328 by subtracting reference data 334 from the target or candidate data 336. In other words, the interference image signal from a target sample is subtracted from the interference image signal from a reference sample (e.g., a rendered image or an adjacent die area image). The difference data 328 may comprise, but is not limited to, a difference image. An initial operation in the processing block 330 may include filtering operations performed on the acquired image or signal data to reduce the background noise relative to the defect signal, for example a conventional low pass filtering scheme. Other filtering methods are known to those of skill in the relevant art and the present invention is intended to cover all such variations. The difference data and techniques described above are intended to be illustrative and not limiting. That is, the scope of the invention is intended to extend to apparatus performing any type of comparison between the sensed image or signal and a reference image or signal.

The image processing block is further configured to generate the complex field information for the sample from the interference image signal of the target or candidate sample. For example, where the acquired image contains spatial fringes, the complex field information derived from analysis of the spatial fringes may include phase, magnitude, or both. Moreover, the complex field information derived from the candidate data 336 may be further processed to provide intensity data, for example, where the reference data 334 stores only intensity data. In contrast, complex field information obtained from temporal phase shifting of the interference image with respect to the image sensor 306 (as further described below), is limited to phase data.

The defect detection may be implemented in the processing block 330 by comparing two images. While often these may be from separate dies, they may include inspection comparisons using patterns on the same die. In die-to-die inspection mode, two areas of the substrate designed to have identical features are compared to each other and any substantial discrepancy is flagged as a defect. This is an example that is often referred to as a random mode inspection. In the die-to-database inspection mode, a defect is detected by comparing the die under test with corresponding graphics information obtained from a computer aided database system from which the die was derived. In frame mode inspection, one pattern on a die is compared to a second pattern on that same die.

The processing block 330 is capable of performing all such comparisons. In one embodiment, following an initial filtering in image processing block, as described above, reference data 334 is compared with candidate data 336 (i.e., from the tested wafer). As noted above, the reference data 334 and candidate data 336 may comprise images but alternatively may be in any other electronic representation format. The reference images or other data format may be stored in a database or determined in a current or previous measurement, depending upon the comparison mode selected. Difference data 338 may be generated as a result of the comparison.

The inspection system 300 may include any suitable combination of the processing block 330, image alignment module 318, and magnifier and zoom module 320. For example, the inspection system may only include a processing block 330 without an image alignment module 318 or magnifier and zoom module 320. These components operate individually or in combination to enhance defect detection by reducing the detection of "false" defects.

In a post data processing block 340, additional processing may be performed on the difference data 338 to better enable identification of defects with respect to pattern noise. Defect inspection based on phase information is extremely sensitive to any variations between the candidate data and the reference data. For example, any variation in film thickness or CD variation will generate "false" defects in the difference data 338. Any process variations may produce difference signals which need to be distinguished from "true" defects.

In one embodiment, for example, known patterns for background noise may be stored and compared with the difference data 338 to help differentiate between pattern noise and actual defects.

Figure 4:
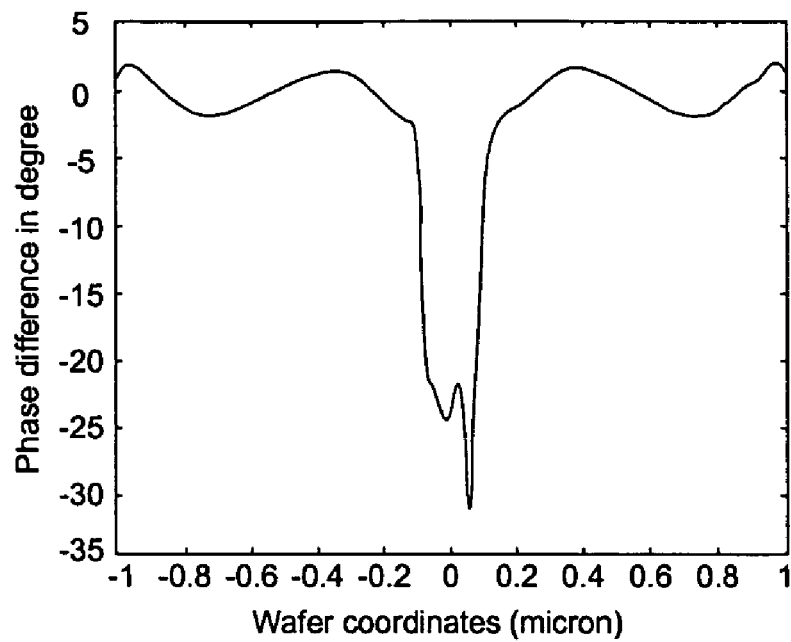
FIG. 4 is a graphical plot illustrating the phase difference caused by a film residual at various wafer coordinate positions as determined in accordance with one embodiment of the present invention.

FIG. 4 is a graphical plot illustrating the phase difference (such as may be generated by the difference data block 338) caused by a 20% film residual at various wafer coordinate positions shown along the x-axis. The phase difference provides a sensitive measure of the defects, i.e., differences between the candidate data 336 and reference data 334. However, in order to differentiate between "false" defects (such as process variations and other pattern noise) and "real" defects such as from incomplete etching further evaluation of the phase difference signals may be performed.

Figure 5:
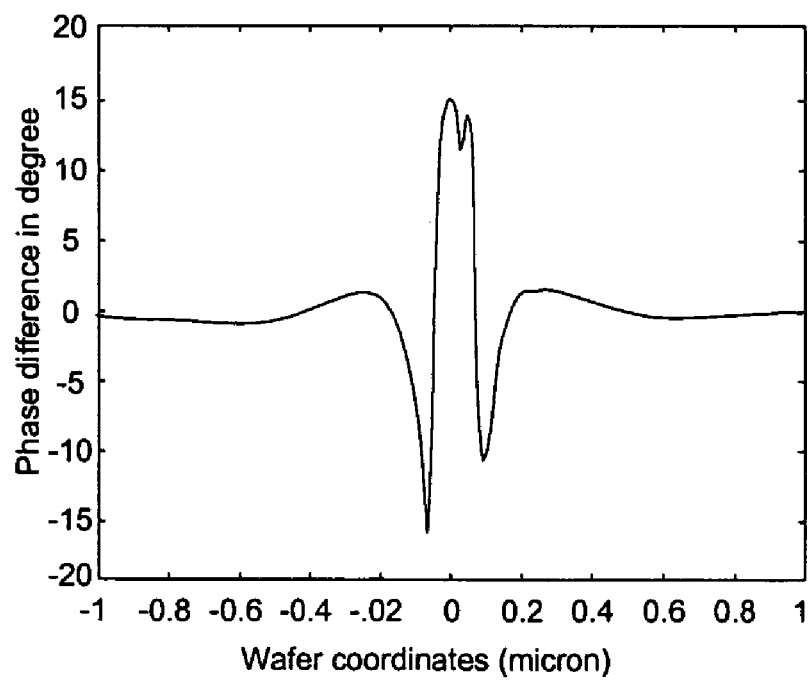
FIG. 5 is a graphical plot illustrating the phase difference caused by a CD variation at various wafer coordinate positions as determined in accordance with one embodiment of the present invention.

FIG. 5 is a graphical plot illustrating the phase difference caused by a 7% CD variation at various wafer coordinate positions shown along the x-axis. Embodiments of the present invention use post data processing to analyze the defect pattern signature to characterize the defects, for example, to differentiate between process variations and film residuals as shown in FIGS. 4 and 5. That is, using the defect pattern signature, "noise" from process variations or other pattern variations may be suppressed. The processing may include, for example, filtering or correlation analysis using prior knowledge of the wafer structure to minimize defects caused by process variations.

The example processing analysis techniques are illustrative and not intended to be limiting. The procedure embodied in block 340 (in FIG. 3A) may be implemented by any suitable combination of hardware and/or software. The techniques may be applied to any difference data generated from difference data block 338 including but not limited to phase, amplitude, and/or fringe modulation data.

Figure 3B:
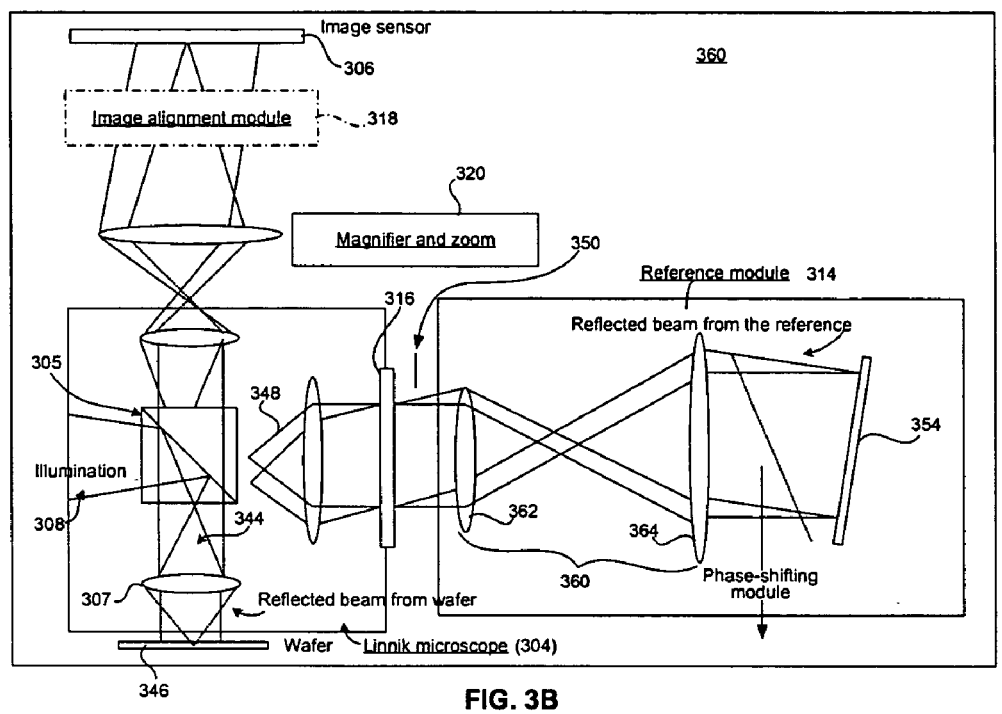
FIG. 3B is a diagrammatic representation illustrating the arrangement of portions of the interferometric inspection system of FIG. 3A in accordance with one embodiment of the present invention.

FIG. 3B is a block diagram illustrating in further detail several of the blocks illustrated in FIG. 3A. As illustrated, the inspection subsystem 360 may include a Linnik microscope 304 with a beam splitter 305, for example a prism positioned to perform a beam splitting function. For example, incident illumination beam 308 may be split into a test beam 344 directed along an optical path towards wafer 346. Reference beam 348 may pass through the bean splitter 305 without reflection and be directed in a separate optical path, towards dichroic surface 316 and reference module 314.

In a further example, the inspection subsystem 360 may be arranged to include an illumination beam 308 generated from a coherent illumination source, and the beam splitter 305 having a special coating designed to reflect a spectral band from the coherent source along the optical path towards the wafer 346 and to permit all other spectral bands in the illumination beam 308 to pass through to the reference module 314. A dichroic surface 316 is placed in this second optical path to serve as a reference mirror for implementing a first operational mode of topographic metrology as described U.S. Pat. No. 4,818,110, which is incorporated by reference herein. However, in one embodiment of the present invention, a complex field inspection may be performed in a second operational mode by selecting the illumination source such that, the reference beam passes through the dichroic surface 316 without reflection.

For example, the coherent 310 and incoherent sources 312 may be selected by providing power only to the selected source. In a further example, power may be provided to the incoherent source 310 if a topographic measurement inspection mode is desired. Preferably, though not necessary, a shutter may be provided between the reference module 314 and the Linnik 304 in lieu of dichroic surface 316 to prevent reflection from the tilted mirror 354 when operating in a topographic inspection mode.

Power may be provided to the coherent source 312 if a complex field inspection mode is desired. Located within the reference module 314 is a tilted mirror 354 for facilitating the creation of spatial fringes in an interference image at the image sensor 306, in accordance with several embodiments of the present invention. In another embodiment, the tilted mirror may be controlled to adjust the optical path difference (OPD) between the test beam and the reference beam to provide multiple measurements for temporal fringe analysis. The reference beam, reflected from the tilted reference mirror 358, further reflects from the mirror located in beamsplitter 305 and is imaged onto image sensor 306. The tilting of the reference mirror permits the creation of an interference pattern at the image sensor 306, for evaluation of the spatial fringes. The reference module 314 may include, in addition to tilted mirror 354, focal relay 360 comprising lenses 362 and 364 to transmit the reference beam to and from the reference mirror 364 without magnification. This configuration, having the tilted mirror 354 located in a separate reference module, provides the advantage of switchably operating in a topographic mode and an inspection mode. In contrast, the Linnik system described in U.S. Pat. No. 4,818,110 places the tilted mirror near the location of the focal point of the Linnik objective and thus does not permit the described dual mode operation. The illumination 308 provided should have sufficient temporal coherence so that the fringe contrast is adequate even with the OPD between the path to the reference mirror 364 and the path to the wafer 346. In one embodiment, the reference module 314 may be removed and a tilted reference mirror placed at approximately location 316, a conjugate plane to the wafer so that the OPD is minimized.

Figure 6A:
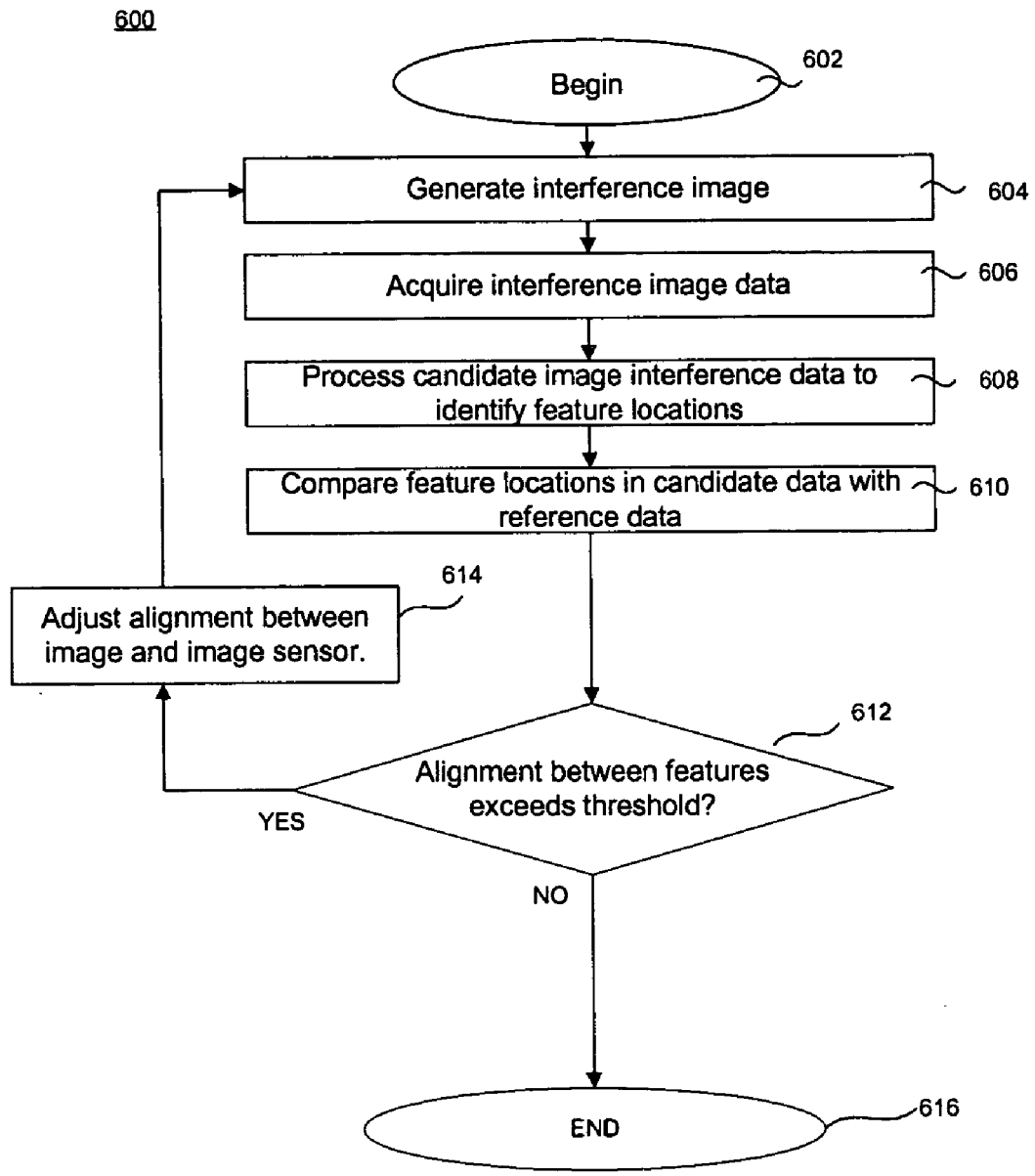
FIG. 6A is a flowchart illustrating a method of aligning an image in accordance with one embodiment of the present invention.

FIG. 6A is a flowchart illustrating an image alignment method 600 in accordance with one embodiment of the present invention. One type of defect inspection, i.e., die-to-die, compares corresponding points (e.g., patterns) on corresponding dies. In order to minimize background noise close matching between the images is necessary. For example, a difference signal or image identifies defects based on the differences between the sample signal or image and the corresponding signal from a reference image. This reference signal or image may be stored (i.e. rendered from a database). The image alignment procedure 600 may be implemented by any suitable combination of hardware and/or software, such as the Linnik microscope configuration, image alignment module, sensor, and processing block as depicted in FIGS. 3A and 3B. The Linnik microscope system is an example of an interferometric inspection microscope for use with embodiments of the present invention but the Linnik configuration is not intended to be limiting.

The process begins at a step 602. Next, at a step 604, the combined reference and test beams, previously split from a single source of illumination, are transmitted onto an image sensor. In the course of transmission from the Linnik microscope to the image sensor, the combined signals may be magnified using suitable hardware. For an example which is not intended to be limiting, the magnifier and zoom module depicted in FIG. 3B may be arranged to provide a magnification from the Linnik to the image sensor such that the desired device line width appears across 4 image pixels.

The image alignment module 318 (as shown in FIG. 3B), in one embodiment, may comprise one or more folding mirrors to adjust the positioning and orientation of the interference image with respect to the image sensor. The image alignment module may be placed in any suitable location to make adjustment of the position and orientation of the interference image onto the image sensor. One suitable location, as illustrated in FIG. 3B, is between the magnification lenses and the image sensor. Next in a step 606, the interference image data is acquired by the image processing block, for example, the processing block 330 illustrated in FIG. 3A. Next, in step 608, the image information is processed to determine the location of selected features on the first die corresponding to selected features on a second die, i.e. the reference die.

The preliminary processing may be performed in any suitable combination of hardware and/or software and is dependent upon the type of interference image generated in the image sensor. For example, spatial fringe techniques produce an interference image on the image sensor, the interference image having visible fringes superimposed on an intensity based image of the pattern on the die. The intensity information alone may be used to determine the position and orientation of the die image on the image sensor. That is, alignment may be performed without performing the additional image processing to identify localized phase and amplitude information for the pattern on the die. Alternatively, the phase and/or amplitude information determined from analyzing the fringes, such as may be performed in one embodiment in processing block 330, may be used to identify the relative position and orientation of the pattern feature with respect to the CCD. In a next step 610, the position and orientation of the feature with respect to the image sensor is compared to the position and orientation of the corresponding feature in the reference image or signal. Next, it is determined in step 612 whether the comparison shows a misalignment exceeding a threshold. If it is determined that the misalignment exceeds the threshold, the alignment of the interference image with respect to the image sensor is adjusted in a step 614.

Figure 6B:
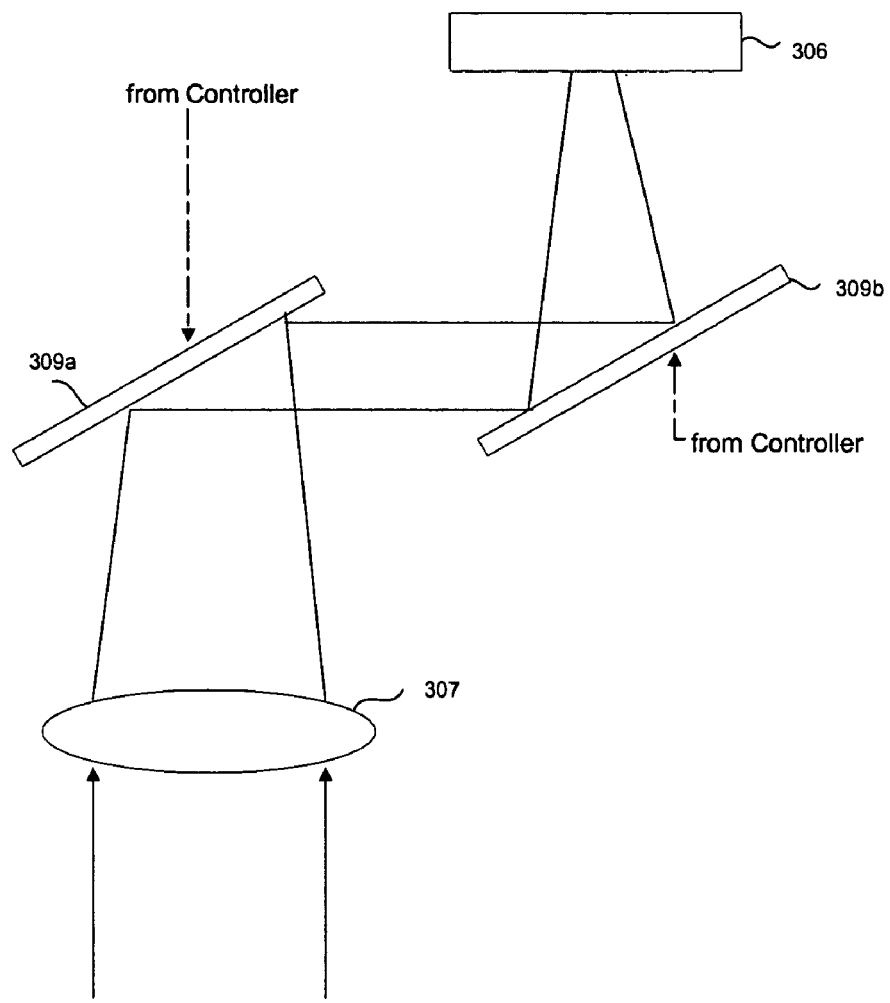
FIG. 6B is an image adjustment apparatus in accordance with one embodiment of the present invention.

Any suitable hardware and software combination may be arranged to perform the alignment determination and control steps described. For example, as illustrated in FIG. 3A, a feedback signal may be transmitted from the processing block to the image alignment module to cause the adjustment of the interference image's position, orientation, or the both of them. Any suitable hardware may be implemented within the image alignment module to perform the adjustment of the interference image. The hardware may comprise, according to one embodiment as illustrated in FIG. 6B, one or more folding mirrors 309a, 309b controlled by a controller in response to a feedback signal from the processing block 330. Such folding mirrors may be located, for example, in the optical path extending from the Linnik objective lens 307 to the image sensor 306. Steps 604 through 614 are repeated until the desired threshold is met. When a satisfactory alignment is determined, the process ends at step 616.

The procedures described may apply both mechanical and digital alignment to achieve the sensitivities selected. For example, an alignment corrected to within $1/100^{th}$ pixel may be selected. That is, the location of the first feature in the interference image with respect to a given pixel from the image representation may be optimally aligned so that the position of the corresponding feature in the reference image differs in location within that image by only $1/100^{th}$ pixel. This goal may be achieved, for example, by performing mechanical adjustment in the image alignment to within $1/10^{th}$ pixel and performing the subpixel alignment by digital processing such as interpolating image values. This example is intended to be illustrative and not limiting. The alignment process of the present invention is intended to cover all ranges of alignment desired, with or without using the digital processing steps to achieve finer alignment.

Figure 7:
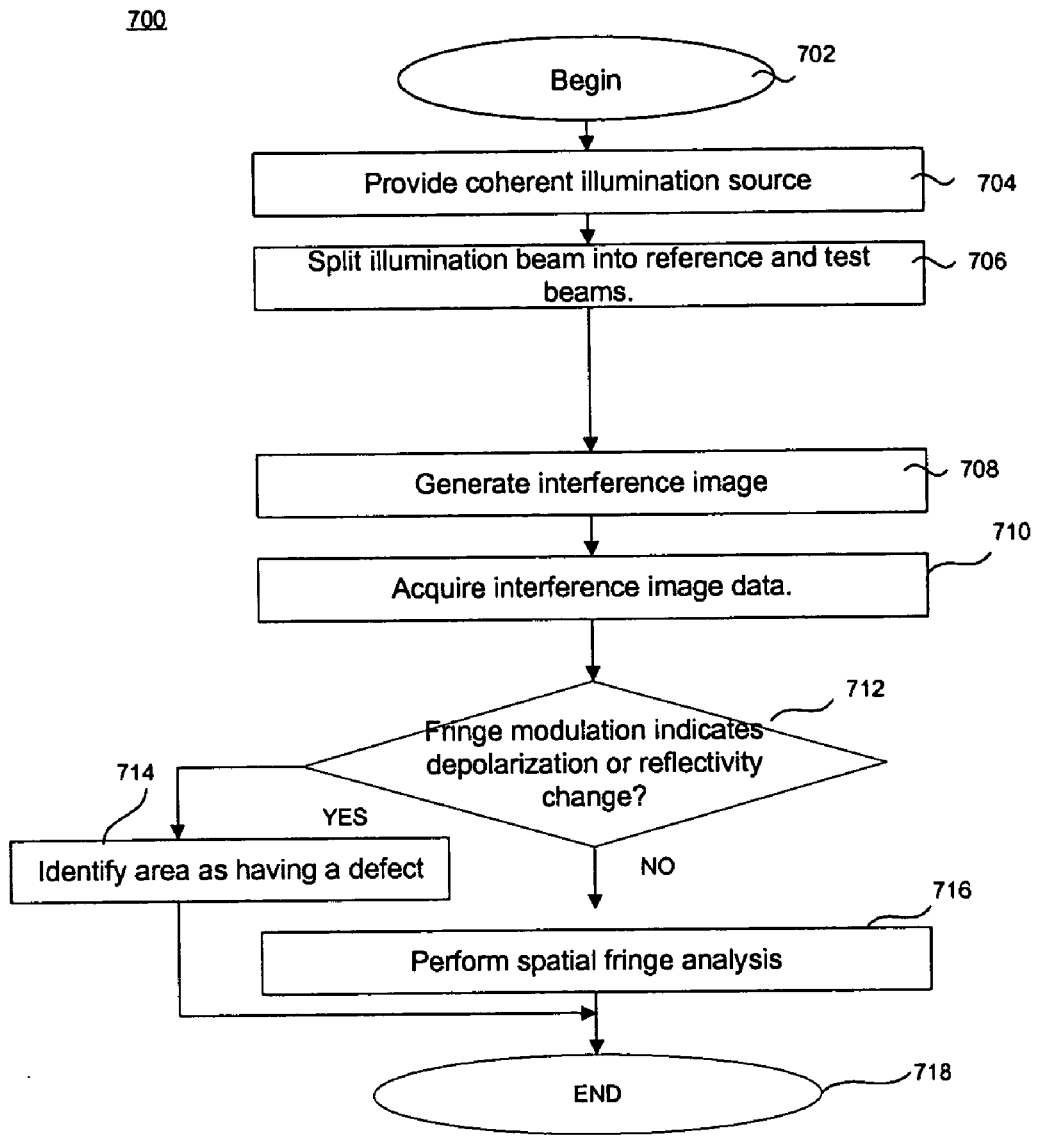
FIG. 7 is a flowchart illustrating a method of performing an interferometric inspection using spatial fringe analysis in accordance with one embodiment of the present invention.

FIG. 7 is a flowchart illustrating steps in the procedure 700 for obtaining complex field information in accordance with one embodiment of the present invention. The process 700 commences at a step 702 and at step 704 illumination is directed towards the Linnik microscope from a coherent source. For example, certain types of laser beams are known to have long coherence lengths and are suitable for use in the process 700. At a step 706, the illumination beam is split into a reference beam and a test beam for later combination into an interference image. The test beam is directed towards the sample, for example, a wafer, reticle, or mask portion, whereas the reference beam is directed along a different optical path in the interferometric system towards a tilted reflective mirror. The tilted reference mirror causes the generation of fringes in the interference image, the fringes being defined as alternating bright and dark bands on the image corresponding to constructive and destructive interference in the image. The spatial fringes permit the derivation of the complex field information, i.e. the phase and amplitude of the signal reflected from the sample.

In specific embodiments, the tilted mirror is located in a separate module, such as the reference module 314 shown in FIGS. 3a and 3B, separated from the Linnik microscope to permit use of the apparatus in dual modes. That is, the Linnik may be operated as a coherence probe for topographic measurement in one mode and in a second mode for measurement of phase and amplitude information from the sample structure. Next the interference image is formed on the image sensor in a step 708 after the separate beams are recombined in the Linnik microscope. Following recombination and projection of the image onto the image sensor, the interference image data is acquired by image processing and filtering software in a step 710. Initially a determination is made as to whether polarization effects have deleteriously affected the fringe information by washing out the fringes in a step 712. In general, portions of an interference image having the fringes "washed out" indicate the presence of defects large enough to cause depolarization.

Once depolarization occurs, the complex field information for that portion cannot be determined. That is, depolarization leads to the reduction in fringe visibility. But, the complex field information, generally designed to discern subtle deflects, is unnecessary in the presence of such information indicating a large defect. If fringe modulation is noted, the processing block identifies the areas as containing a defect. The matching of measured fringe modulations to known fringe modulation patterns may take place in post-data processing block 340 (See FIG. 3A), similar to the pattern matching performed with phase difference measurements as described further above with respect to FIG. 3A. Processing as to the portions of the wafer showing no defects continues.

The filtering and processing may be performed by any suitable combination of hardware and/or software. For example, low pass filtering software may be used to reduce pattern noise before further processing takes place.

Figure 8:
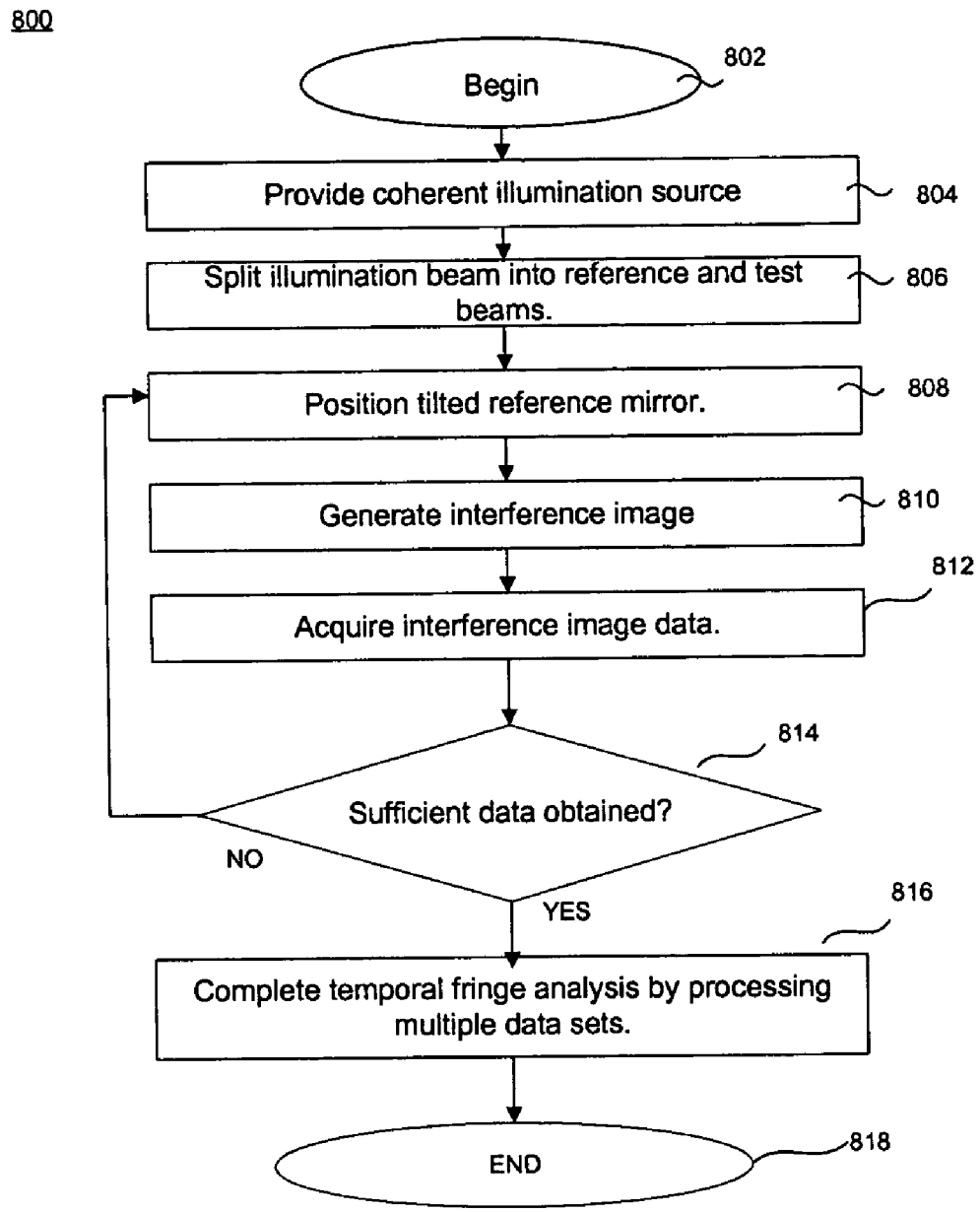
FIG. 8 is a flowchart illustrating a method of performing an interferometric inspection using temporal fringe analysis in accordance with one embodiment of the present invention.

FIG. 8 is a flowchart illustrating a temporal fringe analysis procedure 800 in accordance with another embodiment of the present invention. The procedure 800 may be implemented by any suitable combination of hardware and software, including, for example, the Linnik microscope, reference module, image sensor, illumination sources, and processing block depicted in FIGS. 3A and 3B. The method for temporal fringe analysis 800 commences at a step 802 and at a step 804 a coherent illumination source generates a coherent beam. Suitable illumination sources will have sufficient coherence length such that the optical path difference (OPD) generated in the interferometer is less than the coherent length for the illumination source. Next, at a step 804, the coherent beam is split into a test beam and a reference beam, the test beam directed to the sample and the reference beam directed to a reference surface. The reference surface may be any suitably arranged surface located in a different optical path from the test beam and arranged to create fringes in an interference image on the image sensor. For example, in one embodiment, the reference mirror is tilted and located in a reference module, separated from the Linnik microscope by a partially reflective surface designed and arranged to allow the system to operate in two modes, that is, a first mode for performing topographic inspection and a second mode for detecting complex field information from the sample.

In a next step 808, the tilted reference mirror is positioned to provide a phase information at a first location of the mirror. Positioning may be performed by any suitable mechanism providing accurate control of the translation (i.e., movement of the mirror toward or away from the beam splitting device in the Linnik microscope). For example, a piezo mechanical device such as a piezoelectric transducer (PZT) may be used to provide controlled movement corresponding to the desired positioning of the reference mirror. Following setting of the mirror to its initial position, the image is acquired in a step 810. Determination of phase measurements using the temporal phase shifting techniques provides excellent resolution but requires multiple image acquisitions as opposed to single image acquisitions using spatial fringe techniques. A minimum of three measurements are required to permit the phase information for the sampled surface to be determined. For example, each translation x of the reference mirror along the optical path from the beam splitting device to the reference module will result in a change of 2× in the OPD.

A determination is then made in a step 812 if sufficient image information has been obtained. For example, if the phase shifting algorithm requires images at each of 4 different positions of the reference mirror, a determination is made as to whether 4 images have been acquired and stored. Temporal phase unwrapping algorithms require a minimum of 3 frames (taken at 3 different positions of the PZT mirror) to determine the phase information. This is necessary because of the periodic nature of the phase information contained within the reflected beam. Algorithms using more frames provide the advantage of more accurate phase information, but at the cost of greater time and storage involved in processing. Steps 810 through 812 are repeated until the desired number of images is obtained. Although the temporal phase measurement procedure described provides superior resolution to spatial fringe techniques, it can be seen that the process is slower due to the time for multiple image acquisitions and required movement (i.e., translation) of the reference mirror.

When the desired number of images have been acquired, the inspection process continues in a step 818 where the multiple data images are filtered and processed. This procedure may be incorporated into the overall inspection procedure described with respect to FIG. 2.

The procedures described may be used alone or in combination. For example, inspection of wafers, masks, and reticles, may proceed utilizing the faster spatial fringe analysis in an inspection mode with a second or review mode following the inspection mode to obtained more detailed (i.e., higher resolution information) information regarding defects identified during the inspection mode.

Figure 9:
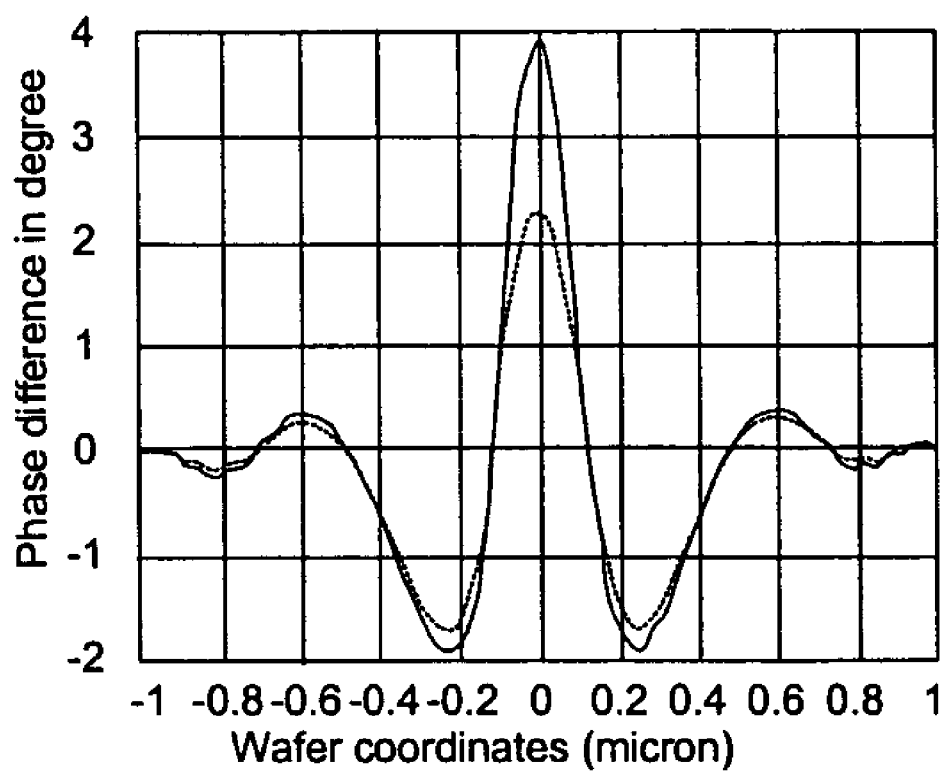
FIG. 9 is a plot illustrating the phase differences generated from inspecting a sample defect at two different planes.

FIG. 9 is graphical plot illustrating the phase intensity differences generated from inspecting a sample defect at two different planes, separated by 50 nm. The phase difference in degrees is shown along the vertical axis. The smaller peak amplitude (i.e., the dotted line) represents an inspection plane not precisely focused to the wafer, whereas the solid line represents the inspection plane focused on the wafer plane of interest. Thus, in order to avoid such adverse effects on phase sensitivity, the present invention in one embodiment uses the inspection system in a topographic inspection mode (i.e., the coherence detection function as described in U.S. Pat. No. 4,818,110, incorporated by reference herein for all purposes) to precisely place the inspection plane. In the system described with reference to FIG. 3A, the white-light source 312 combines with additional illumination relay optics (not shown) to provide a high N.A. illumination to the wafer under inspection. This embodiment permits higher sensitivity in phase measurements by minimizing the signal changes introduced by defocusing from the intended wafer surface.

In an alternative embodiment, two or more image acquisitions may be used to assist in defect detection for different applications and to minimize process noise. That is, by acquiring and storing two different images of the same portion of the wafer sample, for example at two different planes, post processing analysis, such as performed in block 340, may better discriminate between defects and pattern noise. Alternatively, two or more image sensors may be used to inspect the complex field at two different planes, for example by incorporating two sets of optics. Thus, the scope of the invention is not to be limited to a single interferometric microscope module.

By providing a system capable of performing phase-based inspection and intensity-based inspection with minimal changes in the system setup, reduced process time and learning cycles for the system will result. Moreover, both microscopic intensity based and phase type inspection and measurement can be performed during each wafer inspection run. For example, with switching times between the two techniques expected to be limited to only several seconds, a wafer under inspection may be segmented into two different types of region, a first region best inspected with a microscopic technique and a second region best inspected by an interferometric technique.

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention. Accordingly, the present embodiments are to be considered as illustrative and not restrictive, and the invention is not to be limited to the details given herein, but may be modified within the scope and equivalents of the appended claims.

What is claimed is:

1. A method for performing interferometric inspection comprising:

directing an illumination beam through an interferometric microscope to a semiconductor wafer, the illumination beam being split into a test beam and a reference beam in the interferometric microscope;

combining the reference beam reflected from a reference mirror and the test beam reflected from the wafer to generate an interference image having spatial fringes on a time delay integration mode sensor, wherein the reference mirror is adjustable tilted so as to maintain a constant optical path difference between the test beam and the reference beam for a selected portion of the interference image pertaining to a corresponding portion of the wafer.

2. The method for performing interferometric inspection as recited in claim 1, further comprising moving a stage supporting the wafer and synchronizing the movement of the stage with the movement of the interference image on the sensor.

3. The method for performing interferometric inspection as recited in claim 2, wherein synchronizing the movement of the stage with the movement of the interference image comprises controlling the movement of the interference image relative to the sensor by adjusting the movement of the reference mirror in the direction of the axis of the reference beam incident upon the reference mirror.

4. The method for performing interferometric inspection as recited in claim 3, wherein the movement of the reference mirror is adjusted to maintain, as the wafer is moved by the stage, a constant optical path difference between the test beam and the reference beam for a selected portion of the interference image pertaining to a corresponding portion of the wafer.

5. The method for performing interferometric inspection as recited in claim 1, further comprising moving a stage supporting the wafer to induce movement of the interference image relative to the sensor, wherein the spatial fringes are oriented on the sensor so that the spatial fringe lines are aligned in the direction of the induced movement.

6. The method for performing interferometric inspection as recited in claim 1, wherein the image sensor is configured in a time domain integrated mode for both phase based and intensity based measurement.

7. An interferometric inspection apparatus comprising:
    an illumination module configured to generate a first illumination beam for interferometric inspection;
    an interferometric microscope configured to split the illumination beam into a test beam and a reference beam respectively directed to and reflected from a wafer and a reference mirror and to combine the test and reference beams into an interference image having spatial fringe patterns;
    at least one time delay integration mode sensor configured to receive the interference image;
    a movable stage to support the wafer and to induce movement of the interference image relative to the sensor, and
    a processing module operable to induce movement with the movable stage so as to align the spatial fringes on the sensor in the direction of the induced movement.

8. The interferometric inspection apparatus as recited in claim 7, further comprising a movable stage to support the wafer and wherein the apparatus is configured to control the movement of the interference image relative to the sensor by adjusting the movement of the reference mirror in the direction of the axis of the reference beam incident upon the reference mirror.

9. The interferometric inspection apparatus as recited in claim 7, further comprising a movable stage to support the wafer and wherein the apparatus is configured to synchronize the movement of the stage with the movement of the interference image on the sensor.

10. An interferometric inspection system for inspecting semiconductor wafers, the system comprising:
    an interferometric microscope module configured for splitting an illumination beam into a test beam directed to the semiconductor wafer and a reference beam towards a reference mirror, and combining into a combined beam the test beam reflected from the wafer and the reference beam reflected from the reference mirror, the combined beam forming an interference image, wherein the reference mirror is configured to be adjustably tilted with respect to the incident reference beam to generate fringes in the interference image having an orientation different from a dominant direction of a repeating pattern on the wafer; and
    an image sensor configured to receive the interference image and to generate a signal for deriving phase information.

11. The interferometric inspection system as recited in claim 10, wherein the pattern on the wafer is a repeating pattern having a dominant direction and the orientation of the fringes relative to the dominant direction is optimized.

12. The interferometric inspection system as recited in claim 11, wherein the repeating pattern has two dominant directions which are orthogonal to each other and the orientation of the fringes is adjusted to about a 45 degree angle relative to one of two orthogonal directions of the repeating pattern.

13. A method for performing interferometric inspection comprising:
    directing an illumination beam to an interferometric microscope, the illumination beam being split into a test beam and a reference beam in the interferometric microscope, the test beam being reflected from a semiconductor wafer and the reference beam reflected from a reference mirror; and
    combining the reference beam reflected from a reference mirror and the test beam reflected from the wafer to generate an interference image having spatial fringes on a time delay integration mode sensor, wherein the reference mirror is adjusted with respect to the incident reference beam to generate fringes in the interference image having an orientation different from a dominant direction of a repeating pattern on the wafer.

14. The method for performing interferometric inspection as recited in claim 13, wherein the pattern on the wafer is a repeating pattern having a dominant direction and the orientation of the fringes relative to the dominant direction is optimized.

15. The method for performing interferometric inspection as recited in claim 13, wherein the repeating pattern has two dominant directions which are orthogonal to each other and the orientation of the fringes is adjusted to about a 45 degree angle relative to one of two orthogonal directions of the repeating pattern.

* * * * *